United States Patent

Camara et al.

[11] Patent Number: 5,880,332
[45] Date of Patent: Mar. 9, 1999

[54] DNA CONSTRUCTS RELATED TO CAPSANTHIN CAPSORUBIN SYNTHASE, CELLS AND PLANTS DERIVED THEREFROM

[75] Inventors: Bilal Camara; Marcel Kuntz, both of Strasbourg, France

[73] Assignee: Centre National De La Recherche Scientifique, France

[21] Appl. No.: 702,598

[22] PCT Filed: Feb. 17, 1995

[86] PCT No.: PCT/EP95/00584

§ 371 Date: Nov. 25, 1996

§ 102(e) Date: Nov. 25, 1996

[87] PCT Pub. No.: WO95/23863

PCT Pub. Date: Sep. 8, 1995

[30] Foreign Application Priority Data

Mar. 1, 1994 [GB] United Kingdom ............ 94 03943
Mar. 23, 1994 [EP] European Pat. Off. ......... 94 400626

[51] Int. Cl.$^6$ ................. A01H 5/00; C12N 5/14; C12N 15/29; C12N 15/52
[52] U.S. Cl. ............ 800/205; 435/172.3; 435/320.1; 435/419; 536/23.2; 536/23.6; 536/24.5
[58] Field of Search .................. 536/23.2, 23.6, 536/24.1, 24.5; 435/320.1, 419, 172.3; 800/205, 250, DIG. 9, DIG. 44, DIG. 52

[56] References Cited

U.S. PATENT DOCUMENTS

| 5,304,478 | 4/1994 | Bird et al. ............ 435/172.3 |
| 5,365,015 | 11/1994 | Grierson et al. ............ 800/205 |
| 5,429,939 | 7/1995 | Misawa et al. ............ 435/67 |

FOREIGN PATENT DOCUMENTS

| WO-A-9113078 | 5/1991 | WIPO . |
| WO-A-9109128 | 6/1991 | WIPO . |

OTHER PUBLICATIONS

P. Hugueney et al., Biological Abstracts, vol. 95, Abstract No. 9314, 1993.

P. Hugueney et al., Eur. J. Biochem., vol. 209, No. 1, pp. 399–407, 1992.

T. Desprez et al., EMBL Sequence Database Release 38, Acc. No. Z29211, Feb. 1, 1994.

B. Camara et al., Chemical Abstracts, vol. 94, No. 23, Abstract No. 188728, 1981.

B. Camara et al., Biochem. Biophys. Res. Commun., vol. 99, No. 4, pp. 1117–1122, 1981.

H.Y. Yamamoto et al., Chemical Abstracts, vol. 90, No. 1, Abstract No. 2253, 1979.

H.Y. Yamamoto et al., Arch. Biochem. Biophys., vol. 190, No. 2, pp. 514–522, 1978.

B. Camara et al., Chemical Abstracts, vol. 103, No. 7, Abstract No. 50158, 1985.

F. Bouvier et al., The Plant Journal, vol. 6, No. 1, pp. 45–54, Jul. 1994.

B. Camara, Chemical Abstracts, vol. 92, No. 19, Abstract No. 160634, 1980.

R. Fray et al., Plant Molecular Biology, vol. 22, pp. 589–602, 1993.

C.R. Bird et al., Biotechnology, vol. 9, No. 7, pp. 635–639, Jul. 1991.

N. Misawa et al., The Plant Journal, vol. 4, No. 5, pp. 883–840, 1993.

Kunz M. C. annum mRNA for capsanthin/capsorubin synthase. Genbank Accession No. X76165, Nov. 16, 1993.

Stam M, et al. "The silence of genes in transgenic plants." Ann. Bot. 79:3–12, 1997.

Koziel MG, et al. "Optimizing expression of transgenes with an emphasis on post–transcriptional events." Plant Mol. Biol. 32: 393–405, 1996.

Smith CJS, et al. "Antisense RNA inhibition of polygalacturonase gene expression in transgenic tomatoes." Nature 334: 724–726, Aug. 25, 1998.

Primary Examiner—Douglas W. Robinson
Assistant Examiner—Amy J. Nelson
Attorney, Agent, or Firm—Bell, Boyd & Lloyd

[57] ABSTRACT

A DNA construct comprising a DNA sequence homologous to some or all of a sequence encoding a xanthophyll biosynthetic enzyme or a xanthophyll degradative enzyme. In an embodiment the DNA sequence encodes capsanthin-capsorubin synthase (CCS).

15 Claims, 5 Drawing Sheets

```
1                                                                               80
TTTTTTTCACTATACTATATCACCTCCTCTCATAAATAGCCATTATAAATCTTGCATTTTCTCTAATGGAAACCCTTCT
                                                                      M  E  T  L  L     5

160
AAAGCCTTTTCCATCTCCTTTACTTTCCATTCCTACTCCTAACATGTATAGTTTCAAACACAACTCCACTTTTCCAAATC
 K  P  F  P  S  P  L  L  S  I  P  T  P  N  M  Y  S  F  K  H  N  S  T  F  P  N  P     32

240
CAACCAAACAAAAGATTCAAGAAAGTTCCATTATAGAAACAAAAGCAGTACACATTTTGTACGTTTCTTGATTTAGCA
 T  K  Q  K  D  S  R  K  F  H  Y  R  N  K  S  S  T  H  F  C  S  F  L  D  L  A        58

320
CCCACATCAAAGCCACAGTCTTTAGATGTTAACATCTCATGGGTTGATACTGATCTGGACGGGGCTGAATTCGACGTGAT
 P  T  S  K  P  E  S  L  D  V  N  I  S  W  V  D  T  D  L  D  G  A  E  F  D  V  I     85

400
CATCATTGGAACTGGCCCTGCCGGGCTTCGGCTAGCTGAACAAGTTCTAAATATGGTATTAAGGTATGTTGGCGTTGACC
 I  I  G  T  G  P  A  G  L  R  L  A  E  Q  V  S  K  Y  G  I  K  V  C  C  V  D  P    112

480
CTTCACCACTTTCCATGTGGCCAAATAATTATGGTGTTCATATAAGTGATCACCAAGGACTAAGTATTTGGACGACCTA
 S  P  L  S  M  W  P  N  N  Y  G  V  H  I  S  D  H  K  T  K  Y  L  D  R  P  Y        138

540
GATCATAAGTGGCCTGTGAGTTGTGTTCATATAAGTGATCACAAGGACTAAGTATTTGGACGACCATAGTAGAGTAAG
 D  H  K  W  P  V  S  C  V  H  I  S  D  H  K  T  K  Y  L  D  R  P  Y  G  R  V  S    165

620
TAGAAAGAAGTTGAAGTTGAAAATTGTTGAAATAGTGTGTTGAAAATAGAGTGAAGTTTTATAAAGCCAAGGTTTGAAAG
 R  K  K  L  K  L  N  S  C  V  E  N  R  V  K  F  Y  K  A  K  V  L  K  V            192
```

FIG.3A

```
TGAAGCATGAAGAATTTGAGTCTTCGATTGTTGTGATGATGGTAGGAAGATAAGCGGTAGCTTGATTGTTGATGCAAGT    700
 K  H  E  E  F  E  S  S  I  V  C  D  D  G  R  K  I  S  G  S  L  I  V  D  A  S        218
GGCTATGCTAGTGATTTTATAGAGTATGACAAGCCAAGAAACCATGGTTATCAAGTTGCTCATGGGATTTTAGCAGAAGT    780
 G  Y  A  S  D  F  I  E  Y  D  K  P  R  N  H  G  Y  Q  V  A  H  G  I  L  A  E  V     245
TGATAATCATCCATTTGATTTGGATAAAATGATGCTTATGGATTGGAGGGATTCTCATTTAGGTAATGAGCCATATCTGA    840
 D  N  H  P  F  D  L  D  K  M  M  L  M  D  W  R  D  S  H  L  G  N  E  P  Y  L  R     272
GGGTGAAGAATACTAAAGAACCAACATTCTTGTATGCAATGCCATTTGATAGGAATTTGGTAYTCTTGGAAGAGACTTCT    920
 V  K  N  T  K  E  P  T  F  L  Y  A  M  P  F  D  R  N  L  V  F  L  E  E  T  S        298
TTAGTGAGTCGGCCTATGTTATCGTATATGGAAGTGAAAAGAAGGATGTAGCAAGATTAAGACATTTGGGGATCAAAGT    1000
 L  V  S  R  P  M  L  S  Y  M  E  V  K  R  R  M  V  A  R  L  R  H  L  G  I  K  V     325
GAGAAGTGTCCTTGAGGAAGAGAAGTGTGATCACTATGGGAGGACCACTTCCGGCGGATTCCTCAAAATGTTATGGCTA    1080
 R  S  V  L  E  E  E  K  C  V  I  T  M  G  G  P  L  P  R  I  P  Q  N  V  M  A  I     352
TTGGTGGGACTTCAGGGATAGTTCATCCATCGTCTGGGTACATGGTGGCTCGTAGCATGGCATTGGCACCAGTACTGGCT    1140
 G  G  T  S  G  I  V  H  P  S  S  G  Y  M  V  A  R  S  M  A  L  A  P  V  L  A        378
GAGGCCATCGTCGAAAGCCTTGGCTCAACAAGAATGATAAGAGGGTCTCAACTTTACCATAGAGTTTGGAATGGTTGTG    1220
 E  A  I  V  E  S  L  G  S  T  R  M  I  R  G  S  Q  L  Y  H  R  V  W  N  G  L  W     405
```

FIG. 3B

```
                                                                                    1300
GCCTTCGGATAGAAGACGTGTTAGAGAATGTTATTGTTTCGGAATGGAGAGACTTTGTTGAAGCTTGATTTGGAAGGTACTA
 P  S  D  R  R  R  V  R  E  C  Y  C  F  G  M  E  T  L  L  K  L  D  L  E  G  T  R    432
                                                                                    1380
GGAGATTGTTTGATGCTTTCTTTGATGTTGATCCCAAGTACTGGCACGGGTTCCTTTCTTCAAGATTGTCTGTCAAAGAA
 R  L  F  D  A  F  F  D  V  D  P  K  Y  W  H  G  F  L  S  S  R  L  S  V  K  E       458
                                                                                    1440
CTTGCTGTACTCAGTTTGTACCTTTTTGGACATGCCTCTAATTTGGCTAGGTTGGATATTGTTACAAAGTGCACTGTCCC
 L  A  V  L  S  L  Y  L  F  G  H  A  S  N  L  A  R  L  D  I  V  T  K  C  T  V  P    485
                                                                                    1520
CTTGGTTAAACTGCTGGGCAATCTAGCAATAGAGAGCCTTTGAATTAATATGATAGTTTGAAGCACTGTTTTCATTTTA
 L  V  K  L  L  G  N  L  A  I  E  S  L                                              498
                                                                                    1600
ATTTCTTAGGTTATTTCATCTTTTCTCAATGCAAAAGTGAAACAAAAGCTATACACACATTGTCATCGTTGTTCAAACTCA
                                                                                    1676
GACAAGTTTGCCTAGCTCTATGTATTTATCCTTAACATATGTATTCATCAAATTCGAAATATACAATGCATTGGAC(polyA)
```

FIG.3C

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1756 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( i x ) FEATURE:
        ( A ) NAME/KEY: CDS
        ( B ) LOCATION: 67..1560

( x i ) SEQUENCE DESCRIPTION: SEQ ID NO:1:

```
TTTTTTTCA  CTATACTATA  TCACCTCCTC  TCATAAATAG  CCATTATAAA  TCTTGCATTT                 60

TCTCTA ATG GAA ACC CTT CTA AAG CCT TTT CCA TCT CCT TTA CTT TCC                       108
       Met Glu Thr Leu Leu Lys Pro Phe Pro Ser Pro Leu Leu Ser
```

|     |     |     |     |     | 1   |     |     |     |     | 5   |     |     |     |     | 10  |     |     |       |
| --- | --- | --- | --- | --- | --- | --- | --- | --- | --- | --- | --- | --- | --- | --- | --- | --- | --- | ----- |
| ATT | CCT | ACT | CCT | AAC | ATG | TAT | AGT | TTC | AAA | CAC | AAC | TCC | ACT | TTT | CCA |     |     | 156   |
| Ile | Pro | Thr | Pro | Asn | Met | Tyr | Ser | Phe | Lys | His | Asn | Ser | Thr | Phe | Pro |     |     |       |
| 15  |     |     |     |     | 20  |     |     |     |     | 25  |     |     |     |     | 30  |     |     |       |
| AAT | CCA | ACC | AAA | CAA | AAA | GAT | TCA | AGA | AAG | TTC | CAT | TAT | AGA | AAC | AAA |     |     | 204   |
| Asn | Pro | Thr | Lys | Gln | Lys | Asp | Ser | Arg | Lys | Phe | His | Tyr | Arg | Asn | Lys |     |     |       |
|     |     |     |     | 35  |     |     |     |     | 40  |     |     |     |     | 45  |     |     |     |       |
| AGC | AGT | ACA | CAT | TTT | TGT | AGC | TTT | CTT | GAT | TTA | GCA | CCC | ACA | TCA | AAG |     |     | 252   |
| Ser | Ser | Thr | His | Phe | Cys | Ser | Phe | Leu | Asp | Leu | Ala | Pro | Thr | Ser | Lys |     |     |       |
|     |     |     | 50  |     |     |     |     | 55  |     |     |     |     | 60  |     |     |     |     |       |
| CCA | GAG | TCT | TTA | GAT | GTT | AAC | ATC | TCA | TGG | GTT | GAT | ACT | GAT | CTG | GAC |     |     | 300   |
| Pro | Glu | Ser | Leu | Asp | Val | Asn | Ile | Ser | Trp | Val | Asp | Thr | Asp | Leu | Asp |     |     |       |
|     |     | 65  |     |     |     |     | 70  |     |     |     |     | 75  |     |     |     |     |     |       |
| GGG | GCT | GAA | TTC | GAC | GTG | ATC | ATC | ATT | GGA | ACT | GGC | CCT | GCC | GGG | CTT |     |     | 348   |
| Gly | Ala | Glu | Phe | Asp | Val | Ile | Ile | Ile | Gly | Thr | Gly | Pro | Ala | Gly | Leu |     |     |       |
|     | 80  |     |     |     |     | 85  |     |     |     |     | 90  |     |     |     |     |     |     |       |
| CGG | CTA | GCT | GAA | CAA | GTT | TCT | AAA | TAT | GGT | ATT | AAG | GTA | TGT | TGC | GTT |     |     | 396   |
| Arg | Leu | Ala | Glu | Gln | Val | Ser | Lys | Tyr | Gly | Ile | Lys | Val | Cys | Cys | Val |     |     |       |
| 95  |     |     |     |     | 100 |     |     |     |     | 105 |     |     |     |     | 110 |     |     |       |
| GAC | CCT | TCA | CCA | CTT | TCC | ATG | TGG | CCA | AAT | AAT | TAT | GGT | GTT | TGG | GTT |     |     | 444   |
| Asp | Pro | Ser | Pro | Leu | Ser | Met | Trp | Pro | Asn | Asn | Tyr | Gly | Val | Trp | Val |     |     |       |
|     |     |     |     | 115 |     |     |     |     | 120 |     |     |     |     | 125 |     |     |     |       |
| GAT | GAG | TTT | GAA | AAG | TTG | GGA | TTA | GAA | GAT | TGT | CTA | GAT | CAT | AAG | TGG |     |     | 492   |
| Asp | Glu | Phe | Glu | Lys | Leu | Gly | Leu | Glu | Asp | Cys | Leu | Asp | His | Lys | Trp |     |     |       |
|     |     |     | 130 |     |     |     |     | 135 |     |     |     |     | 140 |     |     |     |     |       |
| CCT | GTG | AGT | TGT | GTT | CAT | ATA | AGT | GAT | CAC | AAG | ACT | AAG | TAT | TTG | GAC |     |     | 540   |
| Pro | Val | Ser | Cys | Val | His | Ile | Ser | Asp | His | Lys | Thr | Lys | Tyr | Leu | Asp |     |     |       |
|     |     | 145 |     |     |     |     | 150 |     |     |     |     | 155 |     |     |     |     |     |       |
| AGA | CCA | TAT | GGT | AGA | GTA | AGT | AGA | AAG | AAG | TTG | AAG | TTG | AAA | TTG | TTG |     |     | 588   |
| Arg | Pro | Tyr | Gly | Arg | Val | Ser | Arg | Lys | Lys | Leu | Lys | Leu | Lys | Leu | Leu |     |     |       |
|     | 160 |     |     |     |     | 165 |     |     |     |     | 170 |     |     |     |     |     |     |       |
| AAT | AGT | TGT | GTT | GAA | AAT | AGA | GTG | AAG | TTT | TAT | AAA | GCC | AAG | GTT | TTG |     |     | 636   |
| Asn | Ser | Cys | Val | Glu | Asn | Arg | Val | Lys | Phe | Tyr | Lys | Ala | Lys | Val | Leu |     |     |       |
| 175 |     |     |     |     | 180 |     |     |     |     | 185 |     |     |     |     | 190 |     |     |       |
| AAA | GTG | AAG | CAT | GAA | GAA | TTT | GAG | TCT | TCG | ATT | GTT | TGT | GAT | GAT | GGT |     |     | 684   |
| Lys | Val | Lys | His | Glu | Glu | Phe | Glu | Ser | Ser | Ile | Val | Cys | Asp | Asp | Gly |     |     |       |
|     |     |     | 195 |     |     |     |     | 200 |     |     |     |     | 205 |     |     |     |     |       |
| AGG | AAG | ATA | AGC | GGT | AGC | TTG | ATT | GTT | GAT | GCA | AGT | GGC | TAT | GCT | AGT |     |     | 732   |
| Arg | Lys | Ile | Ser | Gly | Ser | Leu | Ile | Val | Asp | Ala | Ser | Gly | Tyr | Ala | Ser |     |     |       |
|     |     |     | 210 |     |     |     |     | 215 |     |     |     |     | 220 |     |     |     |     |       |
| GAT | TTT | ATA | GAG | TAT | GAC | AAG | CCA | AGA | AAC | CAT | GGT | TAT | CAA | GTT | GCT |     |     | 780   |
| Asp | Phe | Ile | Glu | Tyr | Asp | Lys | Pro | Arg | Asn | His | Gly | Tyr | Gln | Val | Ala |     |     |       |
|     |     | 225 |     |     |     |     | 230 |     |     |     |     | 235 |     |     |     |     |     |       |
| CAT | GGG | ATT | TTA | GCA | GAA | GTT | GAT | AAT | CAT | CCA | TTT | GAT | TTG | GAT | AAA |     |     | 828   |
| His | Gly | Ile | Leu | Ala | Glu | Val | Asp | Asn | His | Pro | Phe | Asp | Leu | Asp | Lys |     |     |       |
|     | 240 |     |     |     |     | 245 |     |     |     |     | 250 |     |     |     |     |     |     |       |
| ATG | ATG | CTT | ATG | GAT | TGG | AGG | GAT | TCT | CAT | TTA | GGT | AAT | GAG | CCA | TAT |     |     | 876   |
| Met | Met | Leu | Met | Asp | Trp | Arg | Asp | Ser | His | Leu | Gly | Asn | Glu | Pro | Tyr |     |     |       |
| 255 |     |     |     |     | 260 |     |     |     |     | 265 |     |     |     |     | 270 |     |     |       |
| CTG | AGG | GTG | AAG | AAT | ACT | AAA | GAA | CCA | ACA | TTC | TTG | TAT | GCA | ATG | CCA |     |     | 924   |
| Leu | Arg | Val | Lys | Asn | Thr | Lys | Glu | Pro | Thr | Phe | Leu | Tyr | Ala | Met | Pro |     |     |       |
|     |     |     |     | 275 |     |     |     |     | 280 |     |     |     |     | 285 |     |     |     |       |
| TTT | GAT | AGG | AAT | TTG | GTA | TTC | TTG | GAA | GAG | ACT | TCT | TTA | GTG | AGT | CGG |     |     | 972   |
| Phe | Asp | Arg | Asn | Leu | Val | Phe | Leu | Glu | Glu | Thr | Ser | Leu | Val | Ser | Arg |     |     |       |
|     |     |     | 290 |     |     |     |     | 295 |     |     |     |     | 300 |     |     |     |     |       |
| CCT | ATG | TTA | TCG | TAT | ATG | GAA | GTG | AAA | AGA | AGG | ATG | GTA | GCA | AGA | TTA |     |     | 1020  |
| Pro | Met | Leu | Ser | Tyr | Met | Glu | Val | Lys | Arg | Arg | Met | Val | Ala | Arg | Leu |     |     |       |
|     |     | 305 |     |     |     |     | 310 |     |     |     |     | 315 |     |     |     |     |     |       |
| AGA | CAT | TTG | GGG | ATC | AAA | GTG | AGA | AGT | GTC | CTT | GAG | GAA | GAG | AAG | TGT |     |     | 1068  |
| Arg | His | Leu | Gly | Ile | Lys | Val | Arg | Ser | Val | Leu | Glu | Glu | Glu | Lys | Cys |     |     |       |

-continued

```
                        320                              325                              330
GTG  ATC  ACT  ATG  GGA  GGA  CCA  CTT  CCG  CGG  ATT  CCT  CAA  AAT  GTT  ATG        1116
Val  Ile  Thr  Met  Gly  Gly  Pro  Leu  Pro  Arg  Ile  Pro  Gln  Asn  Val  Met
335            Ile       340                      345                           350

GCT  ATT  GGT  GGG  ACT  TCA  GGG  ATA  GTT  CAT  CCA  TCG  TCT  GGG  TAC  ATG        1164
Ala  Ile  Gly  Gly  Thr  Ser  Gly  Ile  Val  His  Pro  Ser  Ser  Gly  Tyr  Met
                         355                      360                           365

GTG  GCT  CGT  AGC  ATG  GCA  TTG  GCA  CCA  GTA  CTG  GCT  GAG  GCC  ATC  GTC        1212
Val  Ala  Arg  Ser  Met  Ala  Leu  Ala  Pro  Val  Leu  Ala  Glu  Ala  Ile  Val
               370                           375                      380

GAA  AGC  CTT  GGC  TCA  ACA  AGA  ATG  ATA  AGA  GGG  TCT  CAA  CTT  TAC  CAT        1260
Glu  Ser  Leu  Gly  Ser  Thr  Arg  Met  Ile  Arg  Gly  Ser  Gln  Leu  Tyr  His
          385                           390                      395

AGA  GTT  TGG  AAT  GGT  TTG  TGG  CCT  TCG  GAT  AGA  AGA  CGT  GTT  AGA  GAA        1308
Arg  Val  Trp  Asn  Gly  Leu  Trp  Pro  Ser  Asp  Arg  Arg  Arg  Val  Arg  Glu
     400                           405                      410

TGT  TAT  TGT  TTC  GGA  ATG  GAG  ACT  TTG  TTG  AAG  CTT  GAT  TTG  GAA  GGT        1356
Cys  Tyr  Cys  Phe  Gly  Met  Glu  Thr  Leu  Leu  Lys  Leu  Asp  Leu  Glu  Gly
415                      420                      425                           430

ACT  AGG  AGA  TTG  TTT  GAT  GCT  TTC  TTT  GAT  GTT  GAT  CCC  AAG  TAC  TGG        1404
Thr  Arg  Arg  Leu  Phe  Asp  Ala  Phe  Phe  Asp  Val  Asp  Pro  Lys  Tyr  Trp
                    435                      440                           445

CAC  GGG  TTC  CTT  TCT  TCA  AGA  TTG  TCT  GTC  AAA  GAA  CTT  GCT  GTA  CTC        1452
His  Gly  Phe  Leu  Ser  Ser  Arg  Leu  Ser  Val  Lys  Glu  Leu  Ala  Val  Leu
               450                           455                      460

AGT  TTG  TAC  CTT  TTT  GGA  CAT  GCC  TCT  AAT  TTG  GCT  AGG  TTG  GAT  ATT        1500
Ser  Leu  Tyr  Leu  Phe  Gly  His  Ala  Ser  Asn  Leu  Ala  Arg  Leu  Asp  Ile
          465                           470                      475

GTT  ACA  AAG  TGC  ACT  GTC  CCC  TTG  GTT  AAA  CTG  CTG  GGC  AAT  CTA  GCA        1548
Val  Thr  Lys  Cys  Thr  Val  Pro  Leu  Val  Lys  Leu  Leu  Gly  Asn  Leu  Ala
     480                           485                      490

ATA  GAG  AGC  CTT  TGAATTAATA  TGATAGTTTT  GAAGCACTGT  TTTCATTTTA                     1600
Ile  Glu  Ser  Leu
495

ATTTCTTAGG  TTATTTTCAT  CTTTTCTCAA  TGCAAAAGTG  AAACAAAAGC  TATACACATT                 1660

GTCATCGTTG  TTCAAACTCA  GACAAGTTTG  CCTAGCTCTA  TGTATTTATC  CTTAACATAT                 1720

GTATTCATCA  AATTCGAAAT  ATACAATGCA  TTGGAC                                             1756
```

( 2 ) INFORMATION FOR SEQ ID NO:2:

( i ) SEQUENCE CHARACTERISTICS:
        ( A ) LENGTH: 498 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Glu  Thr  Leu  Leu  Lys  Pro  Phe  Pro  Ser  Pro  Leu  Leu  Ser  Ile  Pro
  1                 5                           10                          15

Thr  Pro  Asn  Met  Tyr  Ser  Phe  Lys  His  Asn  Ser  Thr  Phe  Pro  Asn  Pro
                    20                      25                      30

Thr  Lys  Gln  Lys  Asp  Ser  Arg  Lys  Phe  His  Tyr  Arg  Asn  Lys  Ser  Ser
               35                      40                      45

Thr  His  Phe  Cys  Ser  Phe  Leu  Asp  Leu  Ala  Pro  Thr  Ser  Lys  Pro  Glu
          50                      55                      60

Ser  Leu  Asp  Val  Asn  Ile  Ser  Trp  Val  Asp  Thr  Asp  Leu  Asp  Gly  Ala
 65                      70                      75                           80

Glu  Phe  Asp  Val  Ile  Ile  Ile  Gly  Thr  Gly  Pro  Ala  Gly  Leu  Arg  Leu
```

-continued

```
                                85                           90                           95
Ala  Glu  Gln  Val  Ser  Lys  Tyr  Gly  Ile  Lys  Val  Cys  Cys  Val  Asp  Pro
               100                           105                          110

Ser  Pro  Leu  Ser  Met  Trp  Pro  Asn  Asn  Tyr  Gly  Val  Trp  Val  Asp  Glu
               115                           120                          125

Phe  Glu  Lys  Leu  Gly  Leu  Glu  Asp  Cys  Leu  Asp  His  Lys  Trp  Pro  Val
               130                           135                          140

Ser  Cys  Val  His  Ile  Ser  Asp  His  Lys  Thr  Lys  Tyr  Leu  Asp  Arg  Pro
145                      150                           155                     160

Tyr  Gly  Arg  Val  Ser  Arg  Lys  Lys  Leu  Lys  Leu  Lys  Leu  Leu  Asn  Ser
                    165                      170                          175

Cys  Val  Glu  Asn  Arg  Val  Lys  Phe  Tyr  Lys  Ala  Lys  Val  Leu  Lys  Val
               180                      185                          190

Lys  His  Glu  Glu  Phe  Glu  Ser  Ser  Ile  Val  Cys  Asp  Asp  Gly  Arg  Lys
               195                      200                     205

Ile  Ser  Gly  Ser  Leu  Ile  Val  Asp  Ala  Ser  Gly  Tyr  Ala  Ser  Asp  Phe
          210                      215                     220

Ile  Glu  Tyr  Asp  Lys  Pro  Arg  Asn  His  Gly  Tyr  Gln  Val  Ala  His  Gly
225                           230                      235                     240

Ile  Leu  Ala  Glu  Val  Asp  Asn  His  Pro  Phe  Asp  Leu  Asp  Lys  Met  Met
                    245                      250                     255

Leu  Met  Asp  Trp  Arg  Asp  Ser  His  Leu  Gly  Asn  Glu  Pro  Tyr  Leu  Arg
                    260                      265                     270

Val  Lys  Asn  Thr  Lys  Glu  Pro  Thr  Phe  Leu  Tyr  Ala  Met  Pro  Phe  Asp
               275                      280                          285

Arg  Asn  Leu  Val  Phe  Leu  Glu  Glu  Thr  Ser  Leu  Val  Ser  Arg  Pro  Met
          290                      295                     300

Leu  Ser  Tyr  Met  Glu  Val  Lys  Arg  Arg  Met  Val  Ala  Arg  Leu  Arg  His
305                           310                     315                     320

Leu  Gly  Ile  Lys  Val  Arg  Ser  Val  Leu  Glu  Glu  Lys  Cys  Val  Ile
                         325                      330                     335

Thr  Met  Gly  Gly  Pro  Leu  Pro  Arg  Ile  Pro  Gln  Asn  Val  Met  Ala  Ile
                    340                      345                     350

Gly  Gly  Thr  Ser  Gly  Ile  Val  His  Pro  Ser  Ser  Gly  Tyr  Met  Val  Ala
               355                      360                     365

Arg  Ser  Met  Ala  Leu  Ala  Pro  Val  Leu  Ala  Glu  Ala  Ile  Val  Glu  Ser
     370                      375                     380

Leu  Gly  Ser  Thr  Arg  Met  Ile  Arg  Gly  Ser  Gln  Leu  Tyr  His  Arg  Val
385                      390                     395                          400

Trp  Asn  Gly  Leu  Trp  Pro  Ser  Asp  Arg  Arg  Arg  Val  Arg  Glu  Cys  Tyr
                    405                      410                          415

Cys  Phe  Gly  Met  Glu  Thr  Leu  Leu  Lys  Leu  Asp  Leu  Glu  Gly  Thr  Arg
               420                      425                          430

Arg  Leu  Phe  Asp  Ala  Phe  Phe  Asp  Val  Asp  Pro  Lys  Tyr  Trp  His  Gly
          435                      440                          445

Phe  Leu  Ser  Ser  Arg  Leu  Ser  Val  Lys  Glu  Leu  Ala  Val  Leu  Ser  Leu
     450                      455                     460

Tyr  Leu  Phe  Gly  His  Ala  Ser  Asn  Leu  Ala  Arg  Leu  Asp  Ile  Val  Thr
465                      470                     475                          480

Lys  Cys  Thr  Val  Pro  Leu  Val  Lys  Leu  Leu  Gly  Asn  Leu  Ala  Ile  Glu
                    485                      490                          495

Ser  Leu
```

DNA CONSTRUCTS RELATED TO CAPSANTHIN CAPSORUBIN SYNTHASE, CELLS AND PLANTS DERIVED THEREFROM

BACKGROUND OF THE INVENTION

1. Field of the Invention

The invention relates to novel DNA constructs, plant cells containing the constructs and plants derived therefrom.

In particular it relates to the modification of carotenoid metabolism in plants using DNA constructs.

2. Description of the Prior Art

The modification of plant gene expression has been achieved by several methods. The molecular biologist can choose from a range of known methods to decrease or increase gene expression or to alter the spatial or temporal expression of a particular gene. For example, the expression of either specific antisense RNA or partial (truncated) sense RNA has been utilized to reduce the expression of various target genes in plants (as reviewed by Bird and Ray, 1991, Biotechnology and Genetic Engineering, Reviews 9: 207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al., 1992, Plant Molecular Biology, 19: 69–87).

Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

The carotenoid pathway in plants produces carotenes, lutein, xanthophylls, and pigments such as lycopene. An earlier patent application (published as EP-A-505405) describes a process to modify (inhibit or promote) the synthesis of such compounds in plants using DNA constructs comprising a DNA sequence preferably encoding a phytoene synthase enzyme (which particularly modifies colour of plant parts, especially fruit).

The late steps of carotenoid biosynthesis in plants involve the formation of xanthophylls. Little is known about the enzymology of these steps. No plant xanthophyll biosynthetic enzyme has previously been cloned. In work leading to the present invention we have purified to homogeneity a xanthophyll biosynthetic enzyme from *Capsicum annuum* (pepper) chromoplasts, which catalyzes the conversion of the ubiquitous 5,6-epoxycarotenoids, antheraxanthin and violaxanthin, into capsanthin and capsorubin, respectively. Due to its bifunctionality, this new enzyme has been named capsanthin-capsorubin synthase (CCS).

Both capsanthin and capsorubin are red and give colour to plant tissue. Currently both of these xanthophylls (extracted from paprika) are used as food colourants. Capsanthin and capsorubin are unique to Capsicum fruits and CCS may only be naturally expressed in species of this genus (including peppers, chillies and paprika). However, the immediate precursors for capsanthin and capsorubin (violaxanthin and antheraxanthin) are present in all green tissues.

SUMMARY OF THE INVENTION

The present invention relates to a DNA sequence, containing:

all or part of the nucleotide sequence represented on FIG. 3, coding for a messenger RNA (mRNA), with said mRNA itself coding for a xanthophyll metabolic enzyme represented on FIG. 3, designated by capsanthin-capsorubin synthase (CCS), all or part of any nucleotide sequence which is derived from the above-mentioned sequence represented on FIG. 3, particularly by mutation and/or addition and/or substitution of one or several nucleotide(s), with this derived sequence coding for a mRNA itself coding for the enzyme represented on FIG. 3, or for a protein derived from said enzyme and presenting an enzymatic activity which is equivalent to the activity of the xanthophyll metabolic enzyme of FIG. 3 in plants.

The present invention also relates to a DNA sequence, containing:

all or part of the complementary nucleotidic sequence of the one represented on FIG. 3, and such as defined above, with this complementary sequence coding for an antisense mRNA capable of hybridizing with a mRNA as defined above, or all or part of any DNA sequence which is derived from the above-mentioned complementary sequence, particularly by mutation and/or addition and/or substitution of one or several nucleotide(s), with this derived sequence coding for an antisense mRNA capable of hybridizing with an mRNA as defined above.

The present invention also relates to a mRNA coded by a DNA sequence as defined above, and more particularly coded by the DNA sequence represented on FIG. 3, with said mRNA being capable of coding itself all or part of the xanthophyll metabolic enzyme represented on FIG. 3, or for all or part of a protein derived from this enzyme, and presenting an activity which is equivalent to said enzyme in plants.

The present invention also relates to an antisense mRNA comprising nucleotides which are complementary of all or part of the nucleotides constituting a mRNA as defined above, and capable of hybridizing with said mRNA.

The present invention also relates to an antisense mRNA as defined above, characterized by the fact that it is coded by a DNA sequence as defined above, and by the fact that it is capable of hybridizing with the mRNA coded by the DNA sequence represented on FIG. 3.

The present invention also relates to a CCS present in *Capsicum annuum* cells and such as represented on FIG. 3, or any protein derived from said CCS, particularly by addition and/or suppression and/or substitution of one or several amino-acids, or any fragment from said CCS or derived sequence, with said fragments and derived sequences being capable of presenting an enzymatic activity equivalent to the one of CCS.

The present invention also relates to a nucleotidic sequence coding for the CCS represented on FIG. 3, or any derived sequence or fragment from said CCS, as defined above, with said nucleotidic sequence being characterized by the fact that it corresponds to all or part of the sequence represented on FIG. 3, or to any sequence which is derived from this latter by the degeneracy of the genetic code, and being capable of coding for the CCS, or a derived sequence, or a fragment from said CCS, such as defined above.

The present invention also relates to a complex formed between an antisense mRNA as defined above, and a mRNA as defined above, capable of coding for a CCS in plants.

The present invention also relates to a recombinant DNA characterized by the fact:

that it comprises a DNA sequence as defined above, with said sequence according to claim 1 being inserted in a heterologous sequence capable of coding for mRNA itself capable of coding for CCS.

The present invention also relates to a recombinant DNA characterized by the fact:

that it comprises a DNA sequence which is complementary of a DNA sequence as defined above, inserted in a heterologous sequence, with said complementary DNA sequence being able to code for an antisense mRNA capable of hybridizing with the mRNA coding for a CCS in plants.

The present invention also relates to a DNA recombinant as defined above, characterized by the fact that it comprises the elements necessary to control the expression of the nucleotidic sequence as defined above, or of its complementary sequence as defined above, particularly a promotor and a terminator of the transcription of said sequences.

The present invention also relates to a recombinant vector characterized by the fact that it comprises a recombinant DNA as defined above, integrated in one of its sites of its genome, which are non essential for its replication. The present invention also relates to a process for modifying the production of carotenoid in plants, either by enhancing the production of carotenoid, or by lowering or inhibiting the production of the carotenoid by the plants, with respect to the normal contents of carotenoid produced by plants, said process comprising the transformation of cells of said plants, with a vector as defined above.

The present invention also relates to plants or fragments of plants, particularly fruits, seeds, leaves, petals or cells transformed by incorporation of at least one of the nucleotidic sequences as defined above, into their genome.

According to the present invention, there is provided a DNA construct comprising a DNA sequence homologous to some or all of a sequence encoding a xanthophyll metabolic enzyme. The DNA sequence may be derived from cDNA, from genomic DNA or may be synthesized ab initio. The metabolic enzyme may be a xanthophyll biosynthetic enzyme or a xanthophyll degradative enzyme. Preferably, the DNA sequence encodes capsanthin-capsorubin synthase (CCS).

The purified CCS enzyme is a monomer with a molecular mass of 50 kDa. Antibodies raised against this enzyme allowed the isolation of a full length cDNA clone encoding a capsanthin-capsorubin synthase high molecular weight precursor. The cDNA sequence is shown in FIG. 3. The deduced primary structure reveals the presence of a consensus nucleotide binding site. The capsanthin-capsorubin synthase gene is specifically expressed during chromoplast development in fruits accumulating ketocarotenoids, but not in mutants impaired in this biosynthetic step.

cDNA clones encoding CCS or other xanthophyll metabolic enzyme may be obtained from cDNA libraries using standard methods. Sequences coding for the whole, or substantially the whole, of the mRNA produced by the corresponding gene may thus be obtained. The cDNA so obtained may be sequenced according to known methods.

An alternative source of the DNA sequence is a suitable gene encoding the appropriate xanthophyll metabolic enzyme. This gene may differ from the corresponding cDNA in that introns may be present. The introns are not transcribed into mRNA (or, if so transcribed, are subsequently cut out). Oligonucleotide probes or the cDNA clone may be used to isolate the actual xanthophyll metabolic enzyme gene(s) by screening genomic DNA libraries. Such genomic clones may include control sequences operating in the plant genome. Thus it is also possible to isolate promoter sequences which may be used to drive expression of the enzymes or any other protein. These promoters may be particularly responsive to certain developmental events and environmental conditions. Xanthophyll metabolic enzyme gene promoters may be used to drive expression of any target gene.

A further way of obtaining a xanthophyll metabolic enzyme DNA sequence is to synthesize it ab initio from the appropriate bases, for example using the appropriate cDNA sequence as a guide (for example, FIG. 3 for CCS).

It is clear that xanthophyll metabolic enzyme-encoding sequences may be isolated not only from Capsicum species but from any suitable plant species. Alternative sources of suitable genes include bacteria, yeast, lower and higher eukaryotes.

The xanthophyll metabolic enzyme-encoding sequences may be incorporated into DNA constructs suitable for plant transformation. These DNA constructs may then be used to modify gene expression in plants. "Antisense" or "partial sense" or other techniques may be used to reduce the expression of the xanthophyll metabolic enzyme(s) in plant tissue. The levels of the xanthophyll metabolic enzymes may also be increased; for example, by incorporation of additional enzyme genes. The additional genes may be designed to give either the same or different spatial and temporal patterns of expression in the plant.

The overall level of xanthophyll metabolic enzyme activity and the relative activities of the individual enzymes affect the development and final form of carotenoid content in the plant and thus determine certain characteristics of the plant parts. Modification of xanthophyll metabolic enzyme activity can therefore be used to modify various aspects of plant (including fruit) quality. The activity levels of the xanthophyll metabolic enzymes may be either reduced or increased during development depending on the characteristics desired for the modified plant. Enhancing expression of a biosynthetic enzyme will increase production of the particular xanthophyll product, and inhibiting expression will decrease production. Enhancing expression of a degradative enzyme will decrease levels of the xanthophyll being degraded, while inhibiting expression will increase levels of said xanthophyll.

For example, the down-regulation of CCS biosynthetic enzyme activity in peppers (eg using antisense or sense constructs) will inhibit capsorubin and/or capsanthin production to alter fruit colour. Such down-regulation may result in an accumulation of the immediate precursors of these red pigments, antheraxanthin and violaxanthin, which are orange/yellow. As a further example, over-expression of CCS in Capsicum species may be used to enhance fruit colour.

CCS may also be expressed in cells, tissues and organisms that do not normally produce capsorubin or capsanthin. A DNA sense construct encoding and expressing the functional CCS enzyme may be transformed into any suitable eukaryotic or prokaryotic cell (plant, fungi, algae, bacteria, animal etc). As the immediate precursors for capsanthin and capsorubin are present in all green plant tissue, expression of the CCS enzyme in such tissue leads to capsanthin and capsorubin synthesis. In other cases, the introduction of additional carotenoid biosynthetic genes may be necessary to ensure a supply of the precursors.

CCS could be used to produce capsorubin and/or capsanthin in any higher plant (including Capsicum species, tomato, carrot, cabbage, etc) since the immediate precursors are ubiquitous. This may be useful to change or enhance the colour of the plant or organ depending on the promoter used to drive CCS. It is particularly useful for modifying fruit and vegetable colour but may equally be applied to leaves and other organs.

Capsorubin or capsanthin produced by a eukaryotic or prokaryotic organism expressing a CCS-encoding DNA construct may be extracted for use as a food colourant.

As a further aspect of the invention, a process for the production of capsorubin or capsanthin is provided which comprises transformation of a eukaryotic or prokaryotic cell with a DNA construct encoding and expressing a protein having CCS enzyme activity. It may be necessary to transform the cell with additional constructs expressing enzymes needed to produce the necessary precursors.

A process for the production of violaxanthin or antheraxanthin is further provided which comprises transformation of an eukaryotic or prokaryotic cell with a DNA construct encoding at least part of a protein having CCS enzyme activity so that production of capsorubin or capsanthin is inhibited.

The activity of the xanthophyll metabolic enzyme may be modified either individually or in combination with modification of the activity of another similar or unrelated enzyme. For example, the activity of the CCS enzyme may be modified in combination with modification of the activity of a cell wall enzyme involved in fruit ripening.

Use of the novel xanthophyll metabolic enzyme constructs provides a method for modification of plant characteristics comprising modification of the activity of xanthophyll metabolic enzymes.

According to the present invention there is further provided a DNA construct comprising a DNA sequence homologous to some or all of a sequence encoding a xanthophyll metabolic enzyme under the control of a transcriptional initiation region operative in plants, so that the construct can generate RNA in plant cells.

The characteristics of plant parts (particularly fruit) may be modified by transformation with a DNA construct according to the invention. The invention also provides plant cells containing such constructs; plants derived therefrom showing modified fruit characteristics; and seeds of such plants.

A DNA construct according to the invention may be an "antisense" construct generating "antisense" RNA or "sense" construct (encoding at least part of the functional enzyme) generating "sense" RNA. "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication WO 91/08299) or to over-express the enzyme.

The constructs of the invention may be inserted into plants to regulate the production of xanthophyll metabolic enzymes. The constructs may be transformed into any dicotyledonous or monocotyledonous plant. Depending on the nature of the construct, the production of the enzyme may be increased or reduced, either throughout or at particular stages in the life of the plant. Generally, as would be expected, production of the enzyme is enhanced only by constructs wich express RNA homologous to the substantially complete endogenous enzyme mRNAs. Full-length sense constructs may also inhibit enzyme expression. Constructs containing an incomplete DNA sequence shorter than that corresponding to the complete gene generally inhibit the expression of the gene and production of the enzymes, whether they are arranged to express sense or antisense RNA.

Full-length antisense constructs also inhibit gene expression.

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the xanthophyll metabolic enzyme (making the DNA construct a full or partial antisense construct).

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable xanthophyll metabolic biosynthetic enzyme-encoding sequences is described above. Sequences coding for the whole, or substantially the whole, of the appropriate enzyme may thus be obtained. Suitable lengths of these DNA sequences may be cut out for use by means of restriction enzymes. When using genomic DNA as the source of a partial base sequence for transcription it is possible to use either intron or exon regions or a combination of both.

To obtain constructs suitable for expression of the appropriate xanthophyll metabolic enzyme sequence in plant cells, the cDNA sequence as found in the enzyme cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the enzyme mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional enzyme, the whole of the coding region of the gene is linked to transcriptional control sequences capable of expression in plants.

For example, constructs according to the present invention may be made as follows. A suitable vector containing the desired base sequence for transcription (such as the CCS cDNA clone) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter and the tomato polygalacturonase gene promoter sequence (Bird et al., 1988, Plant Molecular Biology, 11: 651–662) or other developmentally regulated fruit promoters. Suitable terminator sequences include that of the *Agrobacterium tumefaciens* nopaline synthase gene (the nos 3' end).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify enzyme activity only during fruit development and/or ripening. Use of a constitutive promoter will tend to affect enzyme levels and functions in all parts of the plant, while use of a tissue specific promoter allows more selective control of gene expression and affected functions (eg fruit colouration). Thus in applying the invention (for example, to peppers) it may be found convenient to use a promoter that will give expression during fruit development and/or ripening. Thus the antisense or sense RNA is only produced in the organ in which its action is required. Fruit development and/or ripening-specific promoters that could be used include the ripening-enhanced polygalacturonase promoter (International Patent Publication Number WO 92/08798), the E8 promoter (Diekman & Fischer, 1988, EMBO, 7: 3315–3320) and the fruit specific 2A11 promoter (Pear et al., 1989, Plant Molecular Biology, 13: 639–651).

Carotenoid (particularly xanthophyll) content (and hence plant characteristics) may be modified to a greater or lesser extent by controlling the degree of the appropriate xanthophyll metabolic enzyme's sense or antisense mRNA production in the plant cells. This may be done by suitable choice of promoter sequences, or by selecting the number of copies or the site of integration of the DNA sequences that are introduced into the plant genome. For example, the DNA construct may include more than one DNA sequence encoding the xanthophyll metabolic enzyme or more than one recombinant construct may be transformed into each plant cell.

The activity of a first xanthophyll metabolic enzyme may be separately modified by transformation with a suitable DNA construct comprising a DNA sequence encoding the first enzyme. The activity of a second xanthophyll metabolic enzyme may be separately modified by transformation with a suitable DNA construct comprising a DNA sequence encoding the second enzyme. In addition, the activity of both the first and second enzymes may be simultaneaously modified by transforming a cell with two separate constructs: the first comprising a first enzyme-encoding sequence and the second comprising a second enzyme-encoding sequence. Alternatively, a plant cell may be transformed with a single DNA construct comprising both a first enzyme-encoding sequence and a second enzyme-encoding sequence.

It is also possible to modify the activity of the xanthophyll metabolic enzymes while also modifying the activity of one or more other enzymes. For example, the other enzymes may be involved in cell metabolism or in fruit development and ripening. Other cell wall metabolising enzymes that may be modified in combination with xanthophyll metabolic enzymes include but are not limited to: pectin esterase, polygalacturonase, β-galactanase, β-glucanase. Other enzymes involved in fruit development and ripening that may be modified in combination with xanthophyll metabolic enzymes include but are not limited to: ethylene biosynthetic enzymes, other carotenoid biosynthetic enzymes including phytoene synthase, carbohydrate metabolism enzymes including invertase.

Several methods are available for modification of the activity of the xanthophyll metabolic enzymes in combination with other enzymes. For example, a first plant may be individually transformed with a CCS construct and then crossed with a second plant which has been individually transformed with a construct encoding another enzyme. As a further example, plants may be either consecutively or co-transformed with CCS constructs and with appropriate constructs for modification of the activity of the other enzyme(s). An alternative example is plant transformation with a CCS construct which itself contains an additional gene for modification of the activity of the other enzyme(s). The xanthophyll metabolic biosynthetic enzyme constructs may contain sequences of DNA for regulation of the expression of the other enzyme(s) located adjacent to the xanthophyll enzyme sequences. These additional sequences may be in either sense or antisense orientation as described in International Patent Application Publication number WO 93/23551 (single construct having distinct DNA regions homologous to different target genes). By using such methods, the benefits of modifying the activity of the xanthophyll metabolic enzymes may be combined with the benefits of modifying the activity of other enzymes.

A DNA construct of the invention is transformed into a target plant cell. The target plant cell may be part of a whole plant or may be an isolated cell or part of a tissue which may be regenerated into a whole plant. The target plant cell may be selected from any monocotyledonous or dicotyledonous plant species. Suitable plants include any fruit-bearing plant (such as tomatoes, mangoes, peaches, apples, pears, strawberries, bananas, melons, peppers, chillies, paprika). For any particular plant cell, the xanthophyll metabolic enzyme sequence used in the transformation construct may be derived from the same plant species, or may be derived from any other plant species (sufficient sequence similarity to allow modification of related enzyme gene expression).

Constructs according to the invention may be used to transform any plant using any suitable transformation technique to make plants according to the invention. Both monocotyledonous and dicotyledonous plant cells may be transformed in various ways known to the art. In many cases such plant cells (particularly when they are cells of dicotyledonous plants) may be cultured to regenerate whole plants which subsequently reproduce to give successive generations of genetically modified plants. Any suitable method of plant transformation may be used. For example, dicotyledonous plants such as tomato and melon may be transformed by Agrobacterium Ti plasmid technology, such as described by Bevan (1984, Nucleic Acid Research, 12: 8711–8721) or Fillatti et al. (Biotechnology, July 1987, 5: 726–730). Such transformed plants may be reproduced sexually, or by cell or tissue culture.

A process for modifying the production of carotenoids in plants is further provided by transforming such plants with DNA adapted to modify carotenoid biosynthesis and growing such transformed plants or their descendants to produce plant parts (for example leaves, petals or fruit) of modified carotenoid content. Suitable DNA comprises, inter alia, constructs according to the present invention, but other similar constructs affecting other parts of the carotenoid pathway may also be used. Such constructs may be adapted to enhance the production of carotenoids (for example xanthophylls) or inhibit such production by the plant.

As well as colour production, other important functions may be modified by the process of the invention. Thus β-carotene (a precursor of Vitamin A) and other carotenoids are important to human health, and have been claimed to have a protective effect against certain diseases. Food plants may be modified by transformation with the constructs of the invention so that they have a higher content of such compounds: or other plants may be so modified, so that they can act as a source from which such compounds can be extracted. Carotenoids are also believed to have a role in protecting plants against high light intensity damage, so plants with a higher content of such compounds may be of value in combating the effects of any global climate change.

In this way, plants can be generated which have modified colour due to promotion or inhibition of the pathways of carotenoid biosynthesis. In particular, CCS constructs may be used to promote or inhibit the production of the red colour associated with capsorubin or capsanthin. For example, inhibition of this red colour in peppers (eg by transformation with antisense or sense constructs) may give fruit of an attractive shade of orange or yellow. Similar orange/yellow peppers are known, but the present invention provides means of transferring the trait into elite lines without a prolonged breeding programme which might alter other traits at the same time. Promotion of capsorubin or capsanthin production (eg by sense over-expression constructs) may produce peppers of a deeper red colour, which may appear more appetising to the consumer.

The invention may also be used to introduce a red colour into parts of plants other than the fruit. For example, promotion of capsorubin or capsanthin may be brought about by inserting one or more functional copies of the gene cDNA, or of the full-length gene, under control of a promoter functional in plants. If capsorubin or capsanthin are naturally expressed in the plant, the promoter may be selected to give a higher degree of expression than is given by the natural promoter.

Examples of genetically modified plants according to the present invention include fruit-bearing plants. The fruit of such plants may be made more attractive (or at least interesting) by inducing or intensifying a red colour therein. Other plants that may be modified by the process of the invention include tubers such as radishes, turnips and potatoes, as well as cereals such as maize (corn), wheat, barley and rice. Flowers of modified colour, and ornamental grasses either red or reddish overall, or having red seedheads, may be produced.

As already discussed, plants produced by the process of the invention may also contain other recombinant constructs, for example constructs having other effects on fruit ripening. For example fruit of enhanced colour according to the invention may also contain constructs inhibiting the production of enzymes such as polygalacturonase and pectinesterase, or interfering with ethylene production. Fruit containing both types of recombinant construct may be made either by successive transformations, or by crossing two varieties that each contain one of the constructs, and selecting among the progeny for those that contain both.

The invention will now be described by way of example only, with reference to the drawings in which:

BRIEF DESCRIPTION OF THE DRAWINGS

FIG. 3 shows the nucleotide and deduced amino acid sequence of the C. annuum capsanthin-capsorubin cDNA; [A potential dinucleotide binding site (G*GG*A******G) is underlined. Numberings are given in the left margin for amino acids and above the sequence for nucleotides].

DESCRIPTION OF SPECIFIC EMBODIMENTS

Figure 1:
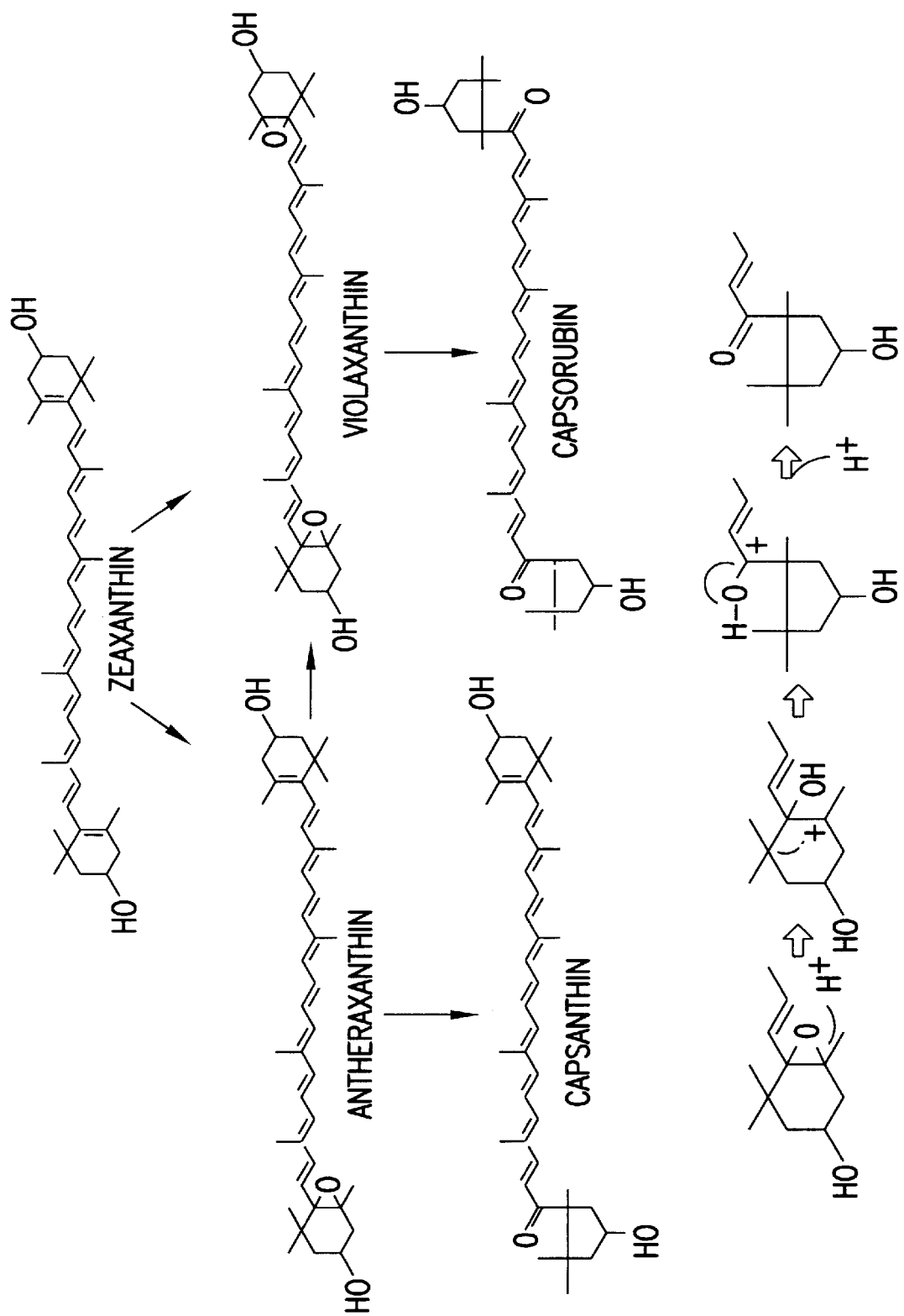
FIG. 1 is a diagram of the proposed reaction and mechanism for the biosynthesis of capsanthin and capsorubin; [conversion of antheraxanthin and violaxanthin into capsanthin and capsorubin; the reaction occurs through a cationic attack and the resulting carbocation is stabilized by ejection of a proton]

To explore the molecular characteristics of the individual plant carotenogenic enzymes, we have used Capsicum annuum chromoplasts as a biological model (Carmara and Monéger, 1982; Camara et al., 1989). This system has allowed the characterization and cloning of geranylgeranyl pyrophosphate synthase (GGPPS) (Dogbo and Camara, 1987; Kuntz et al., 1992), phytoene synthase (Dogbo et al., 1988; Römer et al., 1993) and phytoene-phytofluene desaturase (Hugueney et al., 1992). Concerning the latter steps of the plant carotenogenic pathway which involves the synthesis of xanthophylls, much less is known. Several lines of evidence (Cholnoky et al., 1955; Cholnoky et al. 1955; Davies et al., 1970; Neamtu and Bodea, 1969; Neamtu et al., 1969; Valadon and Mummery, 1977) suggest that epoxyxanthophylls are reactive intermediates involved in the enzymatic interconversion of carotenoids (Costes et al., 1979; Camara, 1980a,b; Camara and Monéger, 1980; Camara and Monéger, 1981) as part of the xanthophyll cycle (Yamamoto, 1979; Yamamoto and Higashi, 1978) and even in the formation of abscisic acid and related derivatives (Rock and Zeevart, 1991; Li and Walton, 1990). However, practically nothing is known about the enzymology of xanthophyll biogenesis.

In ealier studies (Camara, 1980a,b; Camara and Monéger, 1980; Camara and Monéger, 1981), we demonstrated that the ubiquitous 5,6-epoxyxanthophylls, antheraxanthin and violaxanthin, are the direct precursors of capsanthin and capsorubin, respectively, according to the scheme depicted in FIG. 1. The characteristics of these ketoxanthophyll synthases are largely unknown. Further development of a refined in vitro system that is mediating this activity would be a critical step toward defining the molecular characteristics of these xanthophyll biosynthetic enzymes and offer the potential of modifying the later steps of plant carotenogenesis. In Example 1, we describe the properties of such a system, which has allowed the purification of the monomeric and multifunctional xanthophyll biosynthetic enzyme capsanthin-capsorubin synthase (CCS) and the cloning of its cDNA using antibodies directed against this enzyme. We show that the CCS gene is specifically regulated during chloroplast to chromoplast differentiation.

EXAMPLE 1

Subplastidial compartmentation of capsanthin-capsorubin synthase

At the final stage of differentiation, C. annuum chromoplasts are composed of two permanent entities, the soluble fraction (stroma) and the membrane fraction. The latter comprises the plastid envelope as well as a set of new membranes, including achlorophyllous inner membranes and fibrils, both of which are not present in chloroplasts (Spurr and Harris, 1968; Camara and Brangeon, 1981). We have demonstrated previously that isopentenyl pyrophosphate is converted into phytoene by stromal enzymes while the latter steps which involve phytoene desaturation, cyclization and oxidation, are catalysed by membrane-bound enzymes (Camara et al., 1982; Camara et al., 1985). Since the plastid envelope membrane is present in all type of plastids, while the inner achlorophyllous membranes and the fibrils are specifically and strongly triggered during chloroplast to chromoplast differentiation, we hypothesized that the ketoxanthophyll synthase(s) involved in the active biogenesis of capsanthin and capsorubin was most likely associated with the inner achlorophyllous membranes and/or the fibrils which have been shown to be the main site of carotenoid accumulation in C. annuum chromoplasts (Deruère et al., 1994). Therefore, we decided to develop a procedure for the purification of these two chromoplast sub-fractions as described under "Experimental procedures". Electron microscope analysis clearly indicated that these purified fibrils and membrane fractions showed negligible cross-contamination. Previously, we showed that 95% of the chromoplast carotenoids are compartmentalized in the fibrils (Deruère et al., 1994). HPLC analysis of the purified achlorophyllous membranes revealed that qualitatively their major carotenoids are capsanthin and capsorubin while epoxyxanthophylls are minor components.

Figure 2A:
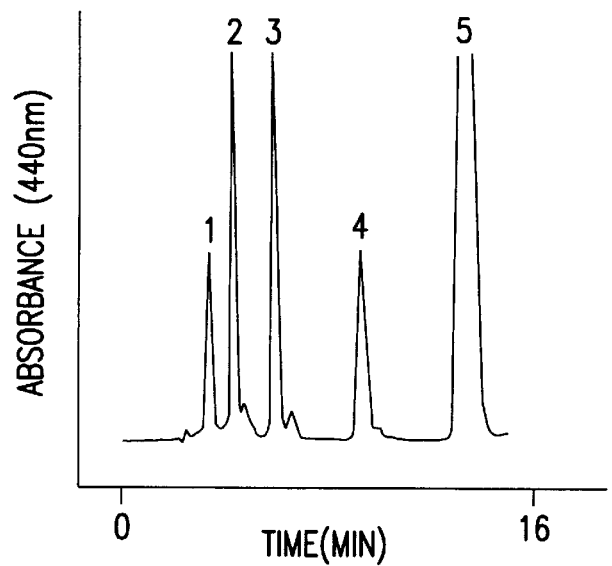
FIG. 2 is a graph of the HPLC analysis of the conversion of antheraxanthin into capsanthin by chromoplast achlorophyllous membranes; [The HPLC profile of the achlorophyllous membrane pigments obtained after incubation and addition of unlabelled carrier antheraxanthin and capsanthin, followed by the distribution of incorporated radioactivity using (b) boiled purified membranes (25 μg) and (c) unboiled isolated membranes (25 μg), separately incubated with ($^{14}$C) antheraxanthin as indicated in Example 1. After 1 h at 28° C., the lipid extract was subjected to HPLC analysis. The position of the different xanthophylls is indicated: (1) neoxanthin; (2) capsorubin; (3) violaxanthin; (4) capsanthin; (5) antheraxanthin].
Figure 2B:
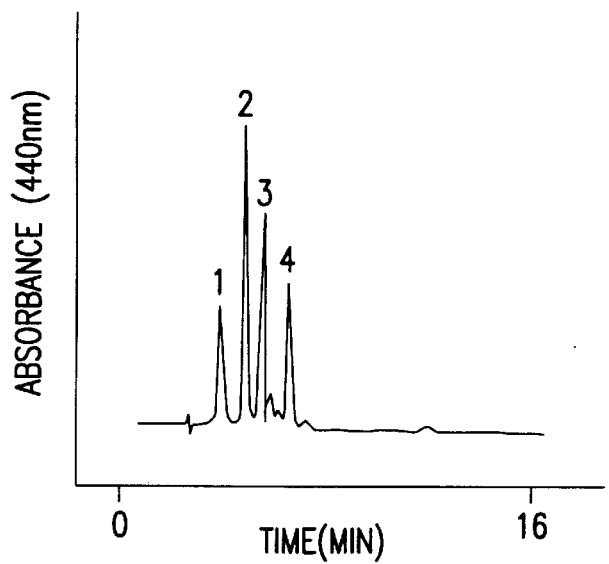
Figure 2C:
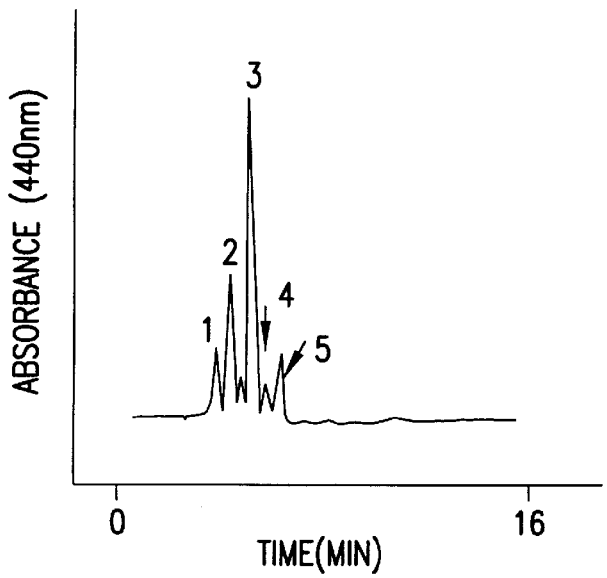

To test their potential ketoxanthophyll synthase activity, both fractions were incubated with labelled antheraxantin. The data displayed in FIG. 2 indicate that this enzymic activity is associated with the purified membrane fraction. Only a negligible activity (less than 2%) was present in the fibrils. We were unable to separate these intraplastidial membranes from the plastid envelope membranes and assess their potential activity. However, plastid envelope membranes or thylakoid membranes prepared from fruit chloroplasts according to Douce and Joyard (1979), were unable to carry out this enzymic conversion (results not shown).

Purification and characteristics of capsanthin-capsorubin synthase

Compared with whole plastid membranes, the purified membrane fraction had a less complex protein pattern. Based on these data, we selected the chromoplast membrane fraction as the starting material for the purification of the ketoxanthophyll synthase(s). Preliminary experiments were carried out to solubilize the ketoxanthophyll synthase(s) from C. annuum membranes. Treatment of the membranes with 1% Triton X-100 or 1% octylglucoside readily solubilized 90% of the ketoxanthophyll synthase initially present in the membrane fraction. Owing to its higher critical micelle concentration, we selected octylglucoside for the subsequent purification steps.

Further analysis of the purified fraction using SDS-PAGE showed one band with an approximate molecular mass of 50 kDa. Also after an additional chromatography on a calibrated column of Sephacryl S-200, a native molecular mass of 60 kDa was determined. Therefore, we conclude that the active enzyme is most probably a monomer. The different purification steps are summarized in Table 1.

The purified enzyme shows a pale yellow colour and gives an intense fluorescence, suggesting that it could be a flavoprotein. However, further spectral analysis and attempts to remove the prosthetic group by acidic pH were inconclusive. Further analysis are required to determine the nature of the prosthetic group.

It has been shown previously that the two 5,6-epoxyxanthophylls antheraxanthin and violaxanthin are the precursors of capsanthin and capsorubin, respectively (Camara, 1980a,b; Camara and Monéger, 1980; Camara and Monéger, 1981). Therefore, an important question remains: does the same enzyme catalyze the formation of both ketoxanthophylls? To address this question, the purified enzyme was incubated with ($^{14}$C) violaxanthin under different experimental conditions as indicated in Table 2. The data obtained indicate that the purified ketoxanthophyll synthase does indeed catalyze the conversion of violaxanthin into capsorubin. Parallel studies aimed at identifying an additional enzyme, immunologically distinct from this ketoxanthophyll synthase, which catalyzes only the conversion of violaxanthin into capsorubin failed. On the basis of this finding, we propose the name capsanthin-capsorubin synthase (CCS) for this ketoxanthophyll synthase which, like other carotenogenic enzymes already characterized from C. annuum, i.e. GGPPS (Dogbo and Camara, 1987), phytoene synthase (Dogbo et al., 1988) and phytoene desaturase (Hugueney et al., 1992), is a multifunctional protein. One can suggest that this type of molecular organization probably results in a better channeling of the substrates which, starting from the prenyl pyrophosphates, are supposed to move from one block of modifying enzymes to another until the final step of the pathway.

Immunological characteristics of capsanthin-capsorubin synthase

Antibodies directed against CCS revealed a single polypeptide of 50 kD specifically localized in the chromoplast membrane fraction. No signal was obtained for chloroplast thylakoid membranes or chloroplast envelope membranes. Only a negligible signal was observed in fibrils.

A solubilized plastid extract was treated with preimmune or anti-CCS serum and the immune complexes were precipitated with protein-A Sepharose according to a previously described procedure (Dogbo et al., 1987). The enzymatic activity of the supernatant fluid was determined. Only anti-CCS antibodies gave a concentration-dependent inhibition (results not shown), thus giving an additional criterium of specificity. Finally, immunocytochemical analysis revealed that CCS is strictly compartmentalized in the plastid. From these data, the serum was considered to be sufficiently specific for developmental studies and for screening a pepper fruit cDNA library.

Isolation of a capsanthin-capsorubin synthase cDNA

Immunoscreening of a C. annuum cDNA library allowed isolation of 2 positive clones of about approximately 300 and 1700 bp, respectively. Subcloning and sequencing of these cDNAs revealed that the 300 bp cDNA is a fragment of the 1700 bp cDNA and that common sequences are completely identical. The larger cDNA possesses an open-reading frame of 498 codons (FIG. 3). The fact that this open-reading frame is preceded by a stop codon in the same frame suggests that this cDNA contains the whole coding sequence.

The deduced amino acid sequence corresponds to a protein of 57 kDa. As expected for a plastid-targeted protein, the NH$_2$-terminus of this protein resembles a typical transit peptide which probably ends before the acidic amino acid-rich region which starts at position 56. Cleavage of the transit peptide a few amino acids before this position would leave a mature protein of approximately 50 kDa, in good agreement with the size of the purified CCS estimated by SDS-PAGE.

A search through the sequence databanks revealed no significant sequence similarity between the deduced CCS sequence and other known sequences, except for a 17 amino acid motif close to the NH$_2$-terminus of the mature protein which resembles a typical dinucleotide binding site (Carothers et al., 1989). Such a motif has also been observed by several authors in the NH$_2$-terminal portion of plant and bacterial phytoene desaturases (Bartley et al., 1991; Hugueney et al., 1992; Misawa et al., 1990; Pecker et al., 1992). Further examination of the CCS sequence revealed several short motifs which are also present in the bacterial lycopene cyclases (not shown), in addition to the motif FLYAXXPXXXXXXXLXE which is present in bacterial zeaxanthin synthase (Misawa et al., 1990). The presence of the latter motif could be due to the fact that zeaxanthin synthase like capsanthin-capsorubin synthase acts on β-cyclohexenyl ring (Camara, 1980a).

Capsanthin-capsorubin synthase is specifically synthesized during chromoplast differentiation Western blot analysis during *C. annuum* development indicated that the synthesis of CCS synthase is specifically and strongly induced during chromoplast differentiation. In addition, RNA gel blot analysis using the CCS cDNA as a probe revealed that the corresponding gene is not expressed in leaves and green fruits from *C. annuum* but only in ripening fruits. During ripening, the expression pattern of the CCS gene appears to be similar to that of the GGPPS gene, namely a strong induction at the early ripening stage which is maintained up to the ripe stage. To confirm this observation, other RNA samples (Kuntz et al., 1992), harvested independently from fruits from a different plant (at a mature green stage, an intermediate ripening stage and a fully ripe stage), were used. Here again, the same pattern of expression was found (data not shown) for both the CCS and the GGPPS gene, namely a strong induction maintained throughout ripening and a decline in the RNA steady-state level later in the fully ripe fruit. These observations suggest that these genes are coexpressed during fruit ripening in *C. annuum*, although the GGPPS gene, unlike the CCS gene, is expressed at low level in all carotenogenic tissues (Kuntz et al., 1992).

Occurrence of capsanthin-capsorubin synthase in fruit colour mutants

To extend the above-mentioned data, we made use of different fruit colour mutants of *C. annuum*. In particular, it was of interest to see whether CCS is absent in the yellow cultivars Jaune de Pignerolle or Golden Summer in which the pericarp turns from green to yellow at the final ripening stage, in the cultivar Sweet Chocolate in which the pericarp turns brown during the final stage of ripening, in the cultivar Alma in which the red colour involves the differentiation of a proplastid into a chromoplast and in the cultivar Permagreen which remains green at the final stage of ripening. Toward this goal, we first analyzed their xanthophyll content by HPLC. The chromatograms obtained indicate the absence of capsanthin and capsorubin in the green and yellow fruit mutants. Similar results were obtained for the cultivar Permagreen at the full ripening stage. In contrast, these ketoxanthophylls are present at the final steps of ripening in the Sweet Chocolate mutant and in the red fruits.

Additional immunological analysis of the green fruits and of yellow mutants revealed that CCS is completely absent. In contrast, CCS is actively synthesized in the Sweet Chocolate mutant and in all red ripe fruits. From these data, we conclude that the yellow fruit mutants and the cultivar Permagreen are specifically impaired in CCS.

RNA samples from ripening fruits of different *C. annuum* varieties were also probed for the presence of the CCS transcript. CCS gene expression could not be detected in the yellow fruit cultivars Jaune de Pignerolle and Golden Summer (even after over-exposure of the autoradiographs). In contrast, the GGPPS gene was found to be expressed in both cultivars. These data are in agreement with the absence of the CCS protein in these cultivars.

The data presented indicate that CCS is a chromoplast-specific protein. We have previously characterized another chromoplast-specific protein that we termed fibrillin and which is the major protein associated with chromoplast fibrils (Deruère et al., 1994). In the fibrillar type of chromoplasts (e.g. in *C. annuum* fruits or *Palisota barteri* fruits, Knoth et al., 1986), fibrils are lipoprotein structures where most of the carotenoids are stored. In contrast, CCS is found in a different chromoplast sub-compartment, namely in membrane structures and most likely in the inner achlorophyllous membranes. These observations suggest that carotenoids once synthesized are discharged into their site of storage (fibrils). Whether this phenomenon involves additional proteins is debatable. Further analysis of the deduced peptide sequence of CCS reveals that the sequence EEKCVIT is similar to the neurofilament consensus sequence EEKVVVTK which is probably involved in several cellular interactions (Hisanaga and Hirokawa, 1988; Shaw, 1992). Therefore, one could suggest that this domain helps in connecting the achlorophyllous membranes network displayed by silver proteinate post-staining and/or mediates a direct interaction between CCS and fibrillin. This data is reminiscent to previous results on cholinesterase, indicating that an enzyme could have a structural role in addition to its catalytic activity (Krejci et al. 1991).

Chromoplast-specific proteins have also been observed by other authors (Winkenbach et al., 1976; Hadjeb et al., 1988; Smirra et al., 1993). One of them, termed ChrA, has a molecular mass of 58 kD and is a carotenoid binding protein (Cervantes-Cervantes et al., 1990). However, when the complete CCS amino acid sequence was compared with the partial amino acid sequence deduced from the published sequence of the ChrA gene (Oren-Shamir et al., 1993), the best homology obtained was only continuous stretch of 10 amino acids. Furthermore, no significant sequence similarity was found between the CCS cDNA and the ChrA gene, which makes it unlikely that CCS is encoded by the published ChrA gene. It should also be mentioned that no transcript corresponding to ChrA could be detected in red *C. annuum* fruits (Oren-Shamir et al., 1993).

Conclusion

A plant xanthophyll biosynthetic enzyme has been isolated which catalyzes two late steps of the carotenogenic pathway, namely the synthesis of capsanthin and capsorubin, and cloned its cDNA. To our knowledge, a previous xanthophyll biosynthetic enzyme has not been described in details, nor its cDNA cloned. The data reported here affords a tool for the molecular analysis of the role of 5,6-epoxyxanthophylls.

Genetics studies (Atkins and Sherrard, 1915; Hurtado-Hernandez and Smith, 1985) have previously assigned the red colour of *C. annuum* fruits to the y locus. Genetic characterization of this locus is currently in progress in order to determine whether y encode(s) CCS or is pleiotropic on the CCS gene.

Experimental procedures

Substrate preparation ($^{14}$C) antheraxanthin and ($^{14}$C) violaxanthin were prepared using *Capsicum annuum* pericarp disk of the yellow cultivar Jaune de Pignerolle incubated overnight with (2-$^{14}$C) potassium mevalonate (60 mCi/mmol, Amersham, France) according to a previously described procedure (Camara, 1980a).

Plant material

Bell pepper plants (*Capsicum annuum* cv. Yolo Wonder) were grown under controlled greenhouse conditions until the fruit ripened, as indicated by the red colour. Several other fruit colour mutants were also grown under the same conditions. These included cultivar Sweet Chocolate which turns into a chocolate colour due to the presence of a chlorophyll retainer gene, cultivar Alma in which the red colour involves proplastid to chromoplast differentiation, yellow cultivars in which the green fruit turns into a deep yellow (cv. Jaune de Pignerolle) or light yellow (cv. Golden Summer) colour, and cultivar Permagreen which remains green at the final stage of ripening.

Plastid subfractionation and enzyme preparations annuum chromoplasts, prepared from 1 kg of red fruit according to a previously described procedure (Camara, 1993), were osmotically lysed by direct resuspension into 100 ml of 50 mM Tris-HCl buffer pH 7.6 containing 1 mM DTT, followed by homogenization using a Potter homogenizer. Twenty ml of the resulting homogenate were layered onto a discontinuous sucrose gradient (identical volumes of 0.5 and 0.9M sucrose) in the same buffer supplemented with 1 mM EDTA. After 1 h centrifugation at 70 000 g at 4° C., using a SW27 rotor (Beckman), the whole fraction above the 0.9M layer was recovered and loaded onto the top of a 0 to 1M linear sucrose gradient in the same buffer, and was centrifuged in a SW27 rotor. After centrifugation at 70 000 g for 12 h at 4° C., the chromoplast fibrils banded at a density of 1.07 g/ml while the purified membrane fraction was recovered at a density corresponding to 1.10 g/ml. The typical yield of purified membranes varied from 400 to 500 µg per kg of fruit pericarp. To 2.8 mg of the purified chromoplast membranes, prepared as described above and resuspended in 5 ml 50 mM Tris-HCl pH 8 (buffer A), were added an equal volume of 2% Triton X-100 or 2% octylglucoside dissolved in the same buffer, in order to solubilize the membrane-bound enzyme. The mixture was stirred at 5° C. for 30 min before centrifugation at 100 000 g for 1 h. The supernatant containing the solubilized enzyme was recovered for further use.

Enzymic assay

The assay mixture in a total volume of 0.25 ml contained: a definite amount of enzyme extract ($^{14}$C) antheraxanthin or ($^{14}$C) violaxanthin (100 000 cpm per µmole) dissolved in 10 µl of ethanol, 250 µg of stromal extract (Hugueney et al., 1992), 0.2 mM NADP$^+$, 0.2 mM NADPH, 1 mM ATP, buffered with 50 mM Tris HCl pH 7.6. After incubation at 28° C. for 30 min, unlabelled xanthophyll standards were added before extraction and analysis of the reaction products by HPLC (Camara, 1985), and determination of the incorporated radioactivity by liquid scintillation.

Enzyme purification

Q-Sepharose chromatography: the solubilisate obtained as described above was batch-adsorbed onto Q-Sepharose (Pharmacia) equilibrated with buffer A containing 0.5% octylglucoside (buffer B). After washing with buffer B containing 25 mM NaCl, the active fraction was eluted in bulk with buffer B containing 0.3M NaCl. After ten-fold dilution, the active fraction was then adsorbed onto a Q-Sepharose column (2×20 cm) equilibrated with buffer B containing 50 mM NaCl. The active fractions were then eluted with a linear salt gradient (0 to 0.3M NaCl) in buffer B. Five ml fractions were collected for the determination of enzyme activity and protein content using the dye binding method (Bio-Rad protein assay kit).

Affigel 501 chromatography: pooled active fractions from the Q-Sepharose column were loaded onto a Affigel 501 column (1×10 cm, Bio-Rad) previously equilibrated with buffer B. The flow through fraction was discarded and after washing the column with ten volumes of buffer B, the active fraction was eluted in bulk by adding 10 mM DTT in buffer B.

Mono P chromatography: the active fraction from the Affigel 501 column was applied onto a Mono P column (HR 5/20, Pharmacia) equilibrated with buffer A. The active fractions were eluted with 12.5% polybuffer 96 (pH 5). Fractions of 1 ml were collected for enzymic assay and protein determination.

Gel filtration: active fractions after the chromatofocusing steps were concentrated by ultrafiltration and applied to a Sephacryl S-200 column (1.5×90 cm, Pharmacia) previously equilibrated with buffer B containing 0.1M NaCl. Fractions of 2.5 ml were collected for enzymic assay and protein determination. The same column was used for the molecular mass determination, using several calibrated molecular mass standards.

Immunoscreening, RNA and DNA techniques

Construction of a λgt11 cDNA library with RNA isolated from a *C. annuum* fruit at an early ripening stage was described previously (Kuntz et al., 1992). Previously described procedures were used for screening, RNA and DNA work (see Kuntz et al., 1992). Hybridizations were performed using standard procedures at 65° C. in 2×SSC. Membranes were then washed at 65° C. in 0.5×SSC.

Microscopy and immunohistochemistry

Pericarp tissue or plastid subfractions were treated as described previously (Camara, 1993; Deruère et al., 1994).

Analytical techniques

The lipid extract was saponified and the xanthophyll fraction obtained after filtration through a silica cartridge was used for HPLC. The pigments were eluted isocratically using methanol/acetone/water (90:17:3), as decribed previously (Camara, 1985). Radioactivity was determined by liquid scintillation counting.

SDS-PAGE and immunoblotting were carried out as described previously (Kuntz et al., 1992) using antibodies directed against the purified enzyme, according to standard techniques. Protein determinations were carried out using a Bio-Rad protein assay kit.

TABLE 1

Purification of ketoxanthophyll synthase from *C. annuum* chromoplast membranes

| Steps | Total protein | Total activity | Specific activity (nmole/h/mg protein) | Recovery (%) |
|---|---|---|---|---|
| Membranes | 2.8 | 294 | 105 | 100 |
| Solubilized membranes | 2 | 252 | 126 | 86 |
| Q-Sepharose | 0.8 | 163 | 204 | 56 |

TABLE 1-continued

Purification of ketoxanthophyll synthase from *C. annuum* chromoplast membranes

| Steps | Total protein | Total activity | Specific activity (nmole/h/mg protein) | Recovery (%) |
|---|---|---|---|---|
| Affigel 501 | 0.4 | 148 | 370 | 50 |
| Mono-P | 0.2 | 85 | 425 | 29 |
| Sephacryl | 0.18 | 79 | 439 | 27 |

TABLE 2

Enzymic conversion of violaxanthin into capsorubin

| Substrate | Radioactivity incorporated into capsorubin by boiled membranes | Radioactivity incorporated into capsorubin by native membranes |
|---|---|---|
| Violaxanthin (15 000 cpm) | 25 | 3200 |
| Violaxanthin (25 000 cpm) | 36 | 6750 |

Purified chromoplast membranes (25 µg) were incubated with the indicated amount of ($^{14}$C) violaxanthin as indicated under Experimental Procedure, before analysis of the radioactivity incorporated in capsorubin. A boiled membrane preparation was used as a control.

The CCS cDNA, or a related DNA fragment as defined in the present invention, can be used as a molecular marker to facilitate plant breeding programs. For instance, isolation of genomic DNA from seedlings produced during plant breeding programs (after sexual or somatic crosses between the same species or different species) and molecular hybridization of the CCS cDNA (or a related DNA fragment) to this genomic DNA can identify those seedlings which possess to CCS gene. This will allow to predict the phenotype of these plants (regarding the fruit colour) without having to wait for fruit formation and ripening.

EXAMPLE 2

Construction of antisense RNA vectors with the CaMV 35S promoter.

A vector is constructed using the sequences corresponding to a fragment of the insert of a CCS cDNA (isolated as shown in example 1). This fragment is synthesized by polymerase chain reaction using synthetic primers. The ends of the fragment are made flush with T4 polymerase and it is cloned into the vector pJR1 which has previously been cut with SmaI. pJR1 (Smith et al., 1988, Nature, 334: 724–726) is a Bin19 (Bevan, 1984, Nucleic Acids Research, 12: 8711–8721) based vector, which permits the expression of the antisense RNA under the control of the CaMV 35S promoter. This vector includes a nopaline synthase (nos) 3' end termination sequence.

Alternatively a vector is constructed using a restriction fragment obtained from a CCS cDNA and cloned into the vectors GA643 (An et al., 1988, Plant Molecular Biology Manual A3: 1–19) or pDH51 (Pietrzak et al., 1986, Nucleic Acids Research, 14: 5875–5869) which has previously been cut with a compatible restriction enzyme(s). A restriction fragment from the CCS/pDH51 clone containing the promoter, the CCS fragment and other pDH51 sequence is cloned into SLJ44026B or SLJ44024B (Jones et al., 1990, Transgenic Research, 1) or Bin19 (Bevan, 1984, Nucleic Acids Research, 12: 8711–8721) which permits the expression of the antisense RNA under control of the CaMV 35S promoter.

After synthesis of the vector, the structure and orientation of the sequences are confirmed by DNA sequence analysis.

EXAMPLE 3

Construction of antisense RNA vectors with a fruit-enhanced promoter.

The fragment of the CCS cDNA that was described in Example 2 is also cloned into the vector pJR3. pJR3 is a Bin19 based vector, which permits the expression of the antisense RNA under the control of the tomato polygalacturonase (PG) promoter. This vector includes approximately 5 kb of promoter sequence and 1.8 kb of 3' sequence from the PG promoter separated by a multiple cloning site.

After synthesis, vectors with the correct orientation of the CCS sequences are identified by DNA sequence analysis.

Alternative fruit-enhanced promoters (such as E8 or 2A11) are substituted for the polygalacturonase promoter in pJR3 to give alternative patterns of expression.

EXAMPLE 4

Construction of truncated sense RNA vectors with the CaMV 35S promoter.

The fragment of the CCS cDNA that was described in Example 2 is also cloned into the vectors described in Example 2 in the sense orientation.

After synthesis, the vectors with the sense orientation of the CCS sequence are identified by DNA sequence analysis.

EXAMPLE 5

Construction of truncated sense RNA vectors with fruit-enhanced promoter.

The fragment of the CCS cDNA that was described in Example 2 is also cloned into the vector pJR3 in the sense orientation.

After synthesis, the vectors with the sense orientation of the CCS sequence are identified by DNA sequence analysis.

Alternative fruit-enhanced promoters (eg E8 or 2A11) are substituted for the polygalacturonase promoter in pJR3 to give alternative patterns of expression.

EXAMPLE 6

Construction of a CCS over-expression vector using the CaMV 35S promoter.

The complete sequence of a CCS cDNA containing a full open-reading frame is inserted into the vectors described in Example 2.

EXAMPLE 7

Construction of a CCS over-expression vector using a fruit-enhanced promoter.

The complete sequence of a CCS cDNA containing a full open-reading frame is inserted into pJR3 or alternatives with different promoters.

EXAMPLE 8

Generation of transformed plants.

Vectors are transferred to *Agrobacterium tumefaciens* LBA4404 (a micro-organism widely available to plant biotechnologists) and are used to transform tomato plants. Transformation of tomato stem segments follow standard protocols (e.g. Bird et al., 1988, Plant Molecular Biology, 11: 651–662). Transformed plants are identified by their ability to grow on media containing the antibiotic kanamycin. Plants are regenerated and grown to maturity. Ripening fruits are analysed for modifications to their ripening characteristics.

EXAMPLE 9

It is to be noted that the CCS cDNA, or restriction fragments of the CCS cDNA, or DNA fragments derived from the CCS cDNA, or oligonucleotides designed from the CCS nucleotide sequence, or oligonucleotides designed from the CCS amino acid sequence can be used to isolate other cDNAs or genomic DNA sequences. These cDNAs or genomic DNAs can be isolated directly from cDNA or genomic libraries using the above-mentioned DNA molecules as hybridization probes. Alternatively, a combination of the above-mentioned oligonucleotides can be used to generate DNA fragments by polymerase chain reactions (PCR).

The isolated DNAs code for enzymes or portion of enzymes which catalyze chemical reactions similar to the one shown in FIG. 1. Examples of such enzymes are cyclases (such as those catalyzing the synthesis of α-carotene or β-carotene), oxidases (introduction of hydroxyl groups, keto groups, aldehyde groups, epoxide groups) and de-epoxidases.

REFERENCES

Armstrong, G. A., Alberti, M., Leach, F. and Hearst, J. E. (1989) Nucleotide sequence organization and nature of the protein products of the carotenoid biosynthesis gene cluster of *Rhodobacter capsulatus*. Molec. Gen. Genet. 216: 254–268.

Atkins, W. R. G. and Sherrard, G. O. (1915) The pigments of fruits in relation to some genetic experiments of *Capsicum annuum* L. Sci. Proc. Roy. Dublin Soc., 14: 328–335.

Bartley, G. E., Vitanen, P. V., Pecker, I., Chamovitz, D., Hirschberg, J. and Scolnik, P. A. (1991) Molecular cloning and expression in photosynthetic bacteria of a soybean cDNA coding for phytoene desaturase, an enzyme of the carotenoid biosynthetic pathway. Proc. Natl. Acad. Sci., 88: 6532–6536.

Camara, B. (1980a) Biosynthesis of keto-carotenoids in *Capsicum annuum* fruits. FEBS Letters, 118: 315–318.

Camara, B. (1980b) Carotenoid biosynthesis: in vitro conversion of violaxanthin to capsorubin by a chromoplast enriched fraction of Capsicum fruits. Biochem. Biophys. Res. Commun., 93: 113–117.

Camara, B. (1985) Prenylation of chlorophyllide a in Capsicum plastids. Methods Enzymol., 110: 274–281.

Camara, B. (1993) Plant phytoene synthase complex: component enzymes, immunology, and biogenesis. Methods Enzymol., 214: 352–365.

Camara, B., Bardat, F. and Monéger, R. (1982) Sites of biosynthesis of carotenoids in Capsicum chromoplasts. Eur. J. Biochem., 127: 255–258.

Camara, B., Bousquet, J., Cheniclet, C., Carde, J. P., Kuntz, M., Evrard, J. L. and Weil, J. H. (1989) Enzymology of isoprenoid biosynthesis and expression of plastid and nuclear genes during chromoplast differentiation in pepper fruits (*Capsicum annuum*). In Physiology Biochemistry and Genetics of Nongreen Plastids. (Boyer, C. D., Shannon, J. C. and Hardison, R. C. eds). Rockville: Am. Soc. Plant Physiol., pp. 141–170.

Camara, B. and Brangeon, J. (1981) Carotenoid metabolism during chloroplast to chromoplast transformation in *Capsicum annuum* fruit. Planta 151: 359–364.

Camara, B., Dogbo, O., d'Harlingue, A., Kleinig, H. and Monéger, R. (1985) Metabolism of plastid terpenoids: lycopene cyclization by Capsicum chromoplast membranes. Biochim. Biophys. Acta., 836: 262–266.

Camara, B. and Monéger, R. (1980) Carotenoid biosynthesis: biogenesis of capsanthin and capsorubin in pepper fruits. (*Capsicum annuum*). In Biogenesis and Function of *Plant Lipids* (Mazliak, P., Benveniste, P., Costes, C. and Douce, R. eds). Elsevier/North-Biomedical Press, pp. 363–367.

Camara, B. and Monéger, R. (1981) Carotenoid biosynthesis: in vitro conversion of antheraxanthin to capsanthin by a chromoplast enriched fraction of Capsicum fruits. Biochem. Biophys. Res. Commun., 99: 1117–1122.

Camara, B. and Monéger, R. (1982) Biosynthetic capabilities and localization of enzymatic activities in carotenoid metabolism of *Capsicum annuum* isolated chromoplasts. Physiol. Veg., 20: 757–773.

Carothers, D. J., Pons, G. and Patel, M. S. (1989) Dihydrolipoamide dehydrogenase: functional similarities and divergent evolution of the pyridine nucleotide-disulfide oxidoreductases. Arch. Biochem. Biophys., 268: 409–425.

Cervantes-Cervantes, M., Hadjeb, N., Newman, L. A. and Price, C. A. (1990) ChrA is a carotenoid-binding protein in chromoplasts of *Capsicum annuum*. Plant Physiol., 93: 1241–1243.

Cholnoky, L., Gyorgyfy, C., Elisabeth, N. and Martha, P. (1956) Function of carotenoids in chlorophyll-containing organs. Nature, 178: 410–411.

Cholnoky, L., Gyorgyfy, K., Nagy, E. and Panczel, M. (1955) Untersuchungen über Carotinoidfarbstoffe. I. Die Farbstoffe des roten Tomaten formigen Paprikas (*Capsicum annuum* varietas *Lycopersiciforme Rubrum*). Acta. Chim. Hung., 6: 143–170.

Costes, C., Burghoffer, C., Joyard, J., Block, M. and Douce, R. (1979) Occurrence and biosynthesis of violaxanthin in isolated chloroplast envelope. FEBS Letters 103: 17–21.

Davies, B. H., Matthews, S. and Kirk, J. T. O. (1970) The nature and biosynthesis of the carotenoids of different colour varieties of *Capsicum annuum*. Phytochemistry, 9: 797–805.

Deruère, J., Römer, S., d'Harlingue, A., Backhaus, R. A., Kuntz, M. and Camara, B. (1994) Fibril assembly and carotenoid over accumulation: a model for supramolecular lipoprotein structures. Plant Cell., 6, (in press).

Dogbo, O., Bardat, F., Laferriere, A., Quennemet, J., Brangeon, J. and Camara, B. (1987) Metabolism of plastid terpenoids. I. Biosynthesis of phytoene in plastid stroma isolated from higher plants. Plant Sci., 49: 89–101.

Dogbo, O. and Camara, B. (1987) Purification of isopentenyl pyrophosphate isomerase and geranylgeranyl pyrophosphate synthase from *Capsicum annuum* chromoplasts by affinity chromatography. Biochim. Biophys. Acta, 920: 140–148.

Dogbo, O., Laferrière, A., d'Harlingue, A. and Camara, B. (1988) Carotenoid biosynthesis: isolation and characterization of a bifunctional enzyme catalyzing the synthesis of phytoene. Proc. Natl. Acad. Sci. USA, 85: 7054–7058.

Douce, R. and Joyard, J. (1979) Isolation and properties of the envelope of spinach chloroplasts. In Plant Organelles, Volume 9 (Reid, E. ed); Chichester: Ellis Horwood Publishers, pp. 47–59.

Hadjeb, N., Gounaris, I. and Price, C. A. (1988) Chromoplast-specific protein in *Capsicum annuum*. Plant Physiol., 88: 42–45.

Hisanaga, S. H. and Hirokawa, N. (1988) Structure of the peripheral domains of neurofilaments revealed by low angle rotary shadowing. J. Mol. Biol., 202: 297–305.

Hugueney, P., Römer, S., Kuntz, M. and Camara, B. (1992) Characterization and molecular cloning of a flavoprotein catalyzing the synthesis of phytofluene and α-carotene in Capsicum chromoplasts. Eur. J. Biochem., 209: 399–407.

Hurtado-Hernandez, H. and Smith, P. G. (1985) Inheritance of mature fruit colour in Capsicum annuum. L. J. Hered., 76: 211–213.

Knoth, R., Hansmann, P. and Sitte, P. (1986) Chromoplasts of Palisota barteri, and the molecular structure of chromoplast tubules. Planta, 168: 167–174.

Krejci, E., Duval, N., Chatonnet, A., Vincens, P. and Massoulié, J. (1991) Cholinesterase-like domains in enzymes and structural proteins: functional and evolutionary relationships and identification of a catalytically essential aspartic. Proc. Natl. Acad. Sci. USA, 88: 6647–6651.

Kuntz, M., Römer, S., Suire, C., Hugueney, P., Weil, J. H., Schantz, R. and Camara, B. (1992) Identification of a cDNA for the plastid-located geranylgeranyl pyrophosphate synthase from Capsicum annuum: correlative increase in enzyme activity and transcript level during fruit ripening. Plant J., 2: 25–34.

Li, Y. and Walton, D. C. (1990) Violaxanthin is an abscisic acid precursor in water-stressed dark grown bean leaves. Plant Physiol., 92: 551–559.

Misawa, N., Nakagawa, M., Kobayashi, K., Yamano, S., Izawa, Y., Nakamura, K. and Harashima, K. (1990) Elucidation of the Erwinia uredovora carotenoid biosynthetic pathway by functional analysis of gene products expressed in Escherichia coli. J. Bacteriol., 172: 6704–6712.

Neamtu, G., Illyes, G. and Bodea, C. (1969) Contributii la biosinteza carotinoidelor. IV Asupra biosintezi carotenoidelor din Aesculus hippocastanum. St. Cerc. Biochim., 12: 77–82.

Neamtu, G. and Bodea, C. (1973) Contributii la biosinteza carotinoidelor. V Biosinteza carotenoidelor din Aesculus rubicunda. Auct. St. Cerc. Biochim., 16: 35–43.

Oren-Shamir, M., Hadjeb, N., Newman, L. A. and Price C. A. (1993) Occurrence of the chromoplast protein ChrA correlates with a fruit-colour gene in Capsicum annuum. Plant. Molec. Biol., 21: 549–554.

Pecker, I., Chamovitz, D., Linden, H., Sandmann, G. and Hirschberg, J. (1992) A single polypeptide catalyzing the conversion of phytoene to α-carotene is transcriptionally regulated during tomato fruit ripening. Proc. Natl. Acad. Sci. USA, 89: 4962–4966.

Rock, C. D. and Zeevaart, J. A. D. (1991) The aba mutant of Arabidopsis thaliana is impaired in epoxy-carotenoid biosynthesis. Proc. Natl. Acad. Sci. USA, 88: 7496–7499.

Römer, S., Hugueney, P., Bouvier, F., Camara, B. and Kuntz, M. (1993) Expression of the genes encoding the early carotenoid biosynthetic enzymes in Capsicum annuum. Biochem. Biophys. Res. Commun., 196: 1414–1421.

Shaw, G. (1992) A neurofilament-specific sequence motif. Trends Biochem. Sci., 17: 345.

Smirra, I., Halevy, A. H. and Vainstein, A. (1993) Isolation and characterization of a chromoplast-specific carotenoid-associated protein from Cucumis sativus corollas. Plant Physiol., 102: 491–496.

Spurr, A. R. and Harris, W. M. (1968) Ultrastructure of chloroplasts and chromoplasts in Capsicum annuum L. Amer. J. Bot., 55: 1210–1224.

Valadon, L. R. G. and Mununery, R. S. (1977) Carotenoids of lillies and red pepper: biogenesis of capsanthin and capsorubin. Z. Pflanzenphysiol., 82: 407–416.

Winkenbach, F., Falk, H., Liedvogel, B. and Sitte, P. (1976) Chromoplasts of Tropaeolum majus L.: isolation and characterization of lipoprotein elements. Planta 128: 23–28.

Yamamoto, H. Y. (1979) Biochemistry of the violaxanthin cycle in higher plants. Pure Appl. Chem., 51: 639–648.

Yamamoto, H. Y. and Higashi, R. M. (1978) Violaxanthin de-epoxidase: lipid composition and substrate specificity. Arch. Biochem. Biophys., 190: 514–522.

EMBL Data Library Accession number X76165 (capsanthin-capsorubin synthase, Capsicum annuum).

---

We claim:

1. An isolated DNA molecule comprising:
(a) the nucleotide sequence of SEQ ID NO:1 or
(b) a nucleotide sequence which encodes the amino acid sequence of SEO ID NO:2.

2. An isolated DNA molecule comprising:
(a) a nucleotide sequence complementary to the sequence of SEQ ID NO:1 or
(b) a nucleotide sequence complementary to sequence which encodes the amino acid sequence of SEQ ID NO:2.

3. An isolated DNA molecule according to claim 1 consisting of (a) or (b) therein.

4. An isolated DNA molecule according to claim 2 consisting of (a) or (b) therein.

5. An isolated mRNA molecule encoded by the isolated DNA molecule according to claim 1.

6. An isolated antisense mRNA molecule encoded by the isolated DNA molecule according to claim 2.

7. An isolated antisense mRNA molecule according to claim 6 that hybridizes with a mRNA encoded by the nucleotide sequence of SEQ ID NO:1.

8. A complex formed between an antisense mRNA according to claim 6 and a mRNA that encodes capsanthin-capsorubin synthase.

9. An isolated nucleic acid molecule that encodes capsanthin-capsorubin synthase comprising the amino acid sequence of SEQ ID NO:2.

10. A recombinant DNA molecule comprising the isolated DNA molecule according to claim 1 or claim 2, operably linked to a heterologous DNA molecule.

11. The recombinant DNA molecule according to claim 10, further comprising a promoter and a terminator of transcription for controlling expression of the isolated DNA molecule.

12. A vector comprising the recombinant DNA molecule of claim 10.

13. A process for modifying the production of carotenoid in plants, either by enhancing the production of carotenoid, or by lowering or inhibiting the production of carotenoid by the plants, with respect to the normal level of carotenoid produced by plants, said process comprising transforming cells of said plants, with a vector according to claim 12.

14. A plant or a fragment of a plant transformed by at least one DNA molecule according to claim 1, wherein said fragment is selected from the group consisting of a fruit, a seed, a leaf, a petal and a cell.

15. A plant or a fragment of a plant transformed by at least one DNA molecule according to claim 2, wherein said fragment is selected from the group consisting of a fruit, a seed, a leaf, a petal and a cell.

* * * * *